United States Patent
Mrue

(10) Patent No.: US 8,603,489 B2
(45) Date of Patent: Dec. 10, 2013

(54) THERAPEUTIC PROTEINS FROM LATEX

(75) Inventor: Fatima Mrue, Goiânia (BR)

(73) Assignee: Pele Nova Biotecnologia S.A., Rodovia (BR)

( * ) Notice: Subject to any disclaimer, the term of this patent is extended or adjusted under 35 U.S.C. 154(b) by 0 days.

(21) Appl. No.: 13/001,288

(22) PCT Filed: Jun. 26, 2009

(86) PCT No.: PCT/BR2009/000185
§ 371 (c)(1),
(2), (4) Date: Mar. 1, 2011

(87) PCT Pub. No.: WO2009/155678
PCT Pub. Date: Dec. 30, 2009

(65) Prior Publication Data
US 2011/0144021 A1    Jun. 16, 2011

(30) Foreign Application Priority Data
Jun. 26, 2008 (BR) ....................................... 0804885

(51) Int. Cl.
*A61K 36/02* (2006.01)
*A61K 35/00* (2006.01)
*A61K 36/00* (2006.01)
*A61K 9/00* (2006.01)
*A61K 31/00* (2006.01)

(52) U.S. Cl.
USPC ..... 424/195.18; 514/13.2; 514/1.1; 514/18.7; 514/16.6; 424/400

(58) Field of Classification Search
None
See application file for complete search history.

(56) References Cited

U.S. PATENT DOCUMENTS

| 5,457,093 | A  |   | 10/1995 | Cini et al. |         |
|-----------|----|---|---------|-------------|---------|
| 6,589,544 | B2 |   | 7/2003  | Leong       |         |
| 6,759,517 | B1 | * | 7/2004  | Cardosa et al. | 530/370 |
| 2004/0171812 | A1 | * | 9/2004 | Mad Arif et al. | 530/370 |

OTHER PUBLICATIONS

Hartree, "Determination of Protein: A Modification of the Lowry Method that Gives a Linear Photometric Response", Analytical Biochemistry, 48, pp. 422-427, 1972.
Fiocchi, "Inflammatory Bowel Disease: Etiology and Pathogenesis", Gastroenterology, 115, pp. 182-205, 1998.
Lowry et al., "Protein Measurement with the Folin Phenol Reagent", Biological Chemistry, 193, pp. 265-275, 1951, www.jbc.org.
Neurath et al., "Antibodies to Interleukin 12 Abrogate Established Experimental Colitis in Mice", The Journal of Experimental Medicine, 182, pp. 1281-1290, 1995.
Bradley et al., "Measurement of Cutaneous Inflammation: Estimation of Neutrophil Content with an Enzyme Marker" The Journal of Investigative Dermatology, 78, pp. 206-209, 1982.
Cheng et al., "Matrine Improves 2,4,6-trinitrobenzene Sulfonic Acid-Induced Colitis in Mice", Pharmacological Research, 53, pp. 202-208, 2006.
Wititsuwannakul et al., "A Lectin From the Bark of the Rubber Tree (Hevea Brasiliensis)", Phytochemistry, 47 (2), pp. 183-187, 1998.
Rogerio et al., "Anti-asthmatic Potential of a D-galactose-binding Lectin From Synadenium Carinatum Latex", Glycobiology, 17 (8), pp. 795-804, 2007.
International Search Report, International Patent Application No. PCT/BR2009/000185, date of actual completion of the search Sep. 22, 2009, 4 pages.
International Preliminary Report on Patentability with Written Opinion, International Patent Application No. PCT/BR2009/000185, date of issuance Jan. 5, 2011, 4 pages.
International Preliminary Report on Patentability with Written Opinion, International Patent Application No. PCT/BR2006/000253, date of issuance May 27, 2008, 5 pages. (corresponds to U.S. Appl. No. 12/094,931).
A.A. Miles et al., "Vascular Reactions to Histamine, Histamine-Liberator and Leukotaxine in the Skin of Guinea-Pigs." The Journal of Physiology, 1952, vol. 118, pp. 228-257.
Jag Wilting et al., "A Modified Chorioallantoic Membrane (CAM) Assay for Qualitative and Qualitative Study of Growth Factors." Anatomy and Embryology, 1991, vol. 183, pp. 259-271.

* cited by examiner

*Primary Examiner* — Chris R Tate
*Assistant Examiner* — Russell Fiebig
(74) *Attorney, Agent, or Firm* — Fitch, Even, Tabin & Flannery, LLP

(57) ABSTRACT

The invention refers to compositions that comprise the protein preparation, obtained from the latex of *Hevea brasiliensis*, in a low concentration. Additionally, the invention refers to the use of the protein preparation or the composition described herein, for the preparation of a medicine to treat chronic inflammatory diseases, and to the method of treating same that uses the aforementioned composition or the protein preparation.

21 Claims, 12 Drawing Sheets

POLYACRYLAMIDE GEL ELECTROPHORESIS WITH SDS OF PEAK 3 (FRACTION FRHB III) TREATED WITH SDS AND REDUCED BY MERCAPTOETHANOL.

Column 3: standard molecular mass (ovoalbumin - 45kDa, carbonic anhydrase - 30 kDa, e cytocrhome c - 12,4 kDa)

Column 2: peak 3 (fraction FrHb III) treated with SDS

Column 1: peak 3 (fraction FrHb III) treated with SDS e 2-mercaptoethanol

Gel 15% in acrylamide

DOSAGE STANDARD CURVE OF CYTOKINE IL-10 OBTAINED THROUGH SERIAL DILUTIONS OF CYTOKINE IL-10

LEVELS OF IL-10 (PG/ML) IN THE SUPERNATANTS OF THE MONONUCLEAR CELL CULTURE CULTIVATED IN THE PRESENCE OF THE CULTURE MEDIUM (BASAL), IN THE PRESENCE OF THE CULTURE MEDIUM WITH THE ADDITION OF CONCAVALINE A (CONA) (50MG/ML), AND IN THE PRESENCE OF THE CULTURE MEDIUM WITH THE ADDITION OF THE CHROMATOGRAPHIC FRACTION OF THE LATEX ($p < 0.05$).

HISTOLOGICAL ALTERATIONS FOUND IN THE COLON OF THE TNBS GROUP IN RELATION TO THE CONTROL GROUP, STAINED BY HE.

A

B

AVERAGE VARIATION OF THE MYELOPEROXIDASE (MPO) ENZYME ACTIVITY BETWEEN THE GROUPS AT THE END OF THE EXPERIMENT (5TH DAY AFTER COLITIS INDUCTION).

THERAPEUTIC PROTEINS FROM LATEX

CROSS REFERENCE TO RELATED APPLICATIONS

This application is a national phase application of International Application No. PCT/BR2009/000185, filed Jun. 26, 2009, claiming priority to Brazilian Application No. PI 08048854-1, filed Jun. 26, 2008, which applications are incorporated by reference herein in their entirety.

FIELD OF THE INVENTION

The present invention generically refers to a protein preparation derivative of latex from the plant Hevea brasiliensis and to compositions containing it, in low concentration.

Additionally, the present invention refers to the use of the said preparation and of said composition in the preparation of a medicine to treat acute or chronic inflammatory diseases, particularly, intestinal inflammatory diseases (IID) and systemic inflammatory response syndrome (SIRS), as well as a method of treating said diseases, using the aforementioned protein preparation, or the composition with the protein preparation of the present invention.

BACKGROUND OF THE INVENTION

Intestinal inflammatory diseases (IID) are a family of chronic, idiopathic, recurrent and tissue-destructive diseases, characterized by the dysfunction of mucous cells T $CD4^+$ and $CD8^+$, altered production of cytokines and cellular inflammation, leading to prolonged and sometimes irreversible damage of the gastrointestinal function and structure, more precisely, in the distal portion of the large intestine and colonic mucosa. The main IID that occurs in humans are subdivided into two phenotypes: Crohn's disease and ulcerative colitis.

Crohn's disease is a chronic disease characterized by transmural and granulomatous inflammation, which can cause inflammation in any segment of the digestive tract, as a result of disorderly immune responses against intraluminal antigens derivatives of the commensal bacterial flora in genetically susceptible individuals.

Ulcerative colitis occurs as a consequence of a recurrent acute or chronic intestinal inflammatory disease and is confined to the entire intestine, starting in the rectum and progressing, apparently, continuously affecting other intestinal portions.

Both Crohn's disease and ulcerative colitis are accompanied by clinical symptoms such as diarrhea, rectal prolapse, weight loss and abdominal pains, and are histologically characterized by inflammation and ulceration of the colonic mucosa.

Studies on the pathogenesis of IID and the potential therapeutic agents for treating these diseases has been of major importance over recent decades. It is known that the severity of the intestinal inflammatory process may be a consequence of the decrease of the regulation mechanisms involved in the homeostasis of the intestinal mucosa, and many of these processes have been attributed to the deficiency of the production of one of the main cytokines involved in regulating inflammatory responses of the organism, IL-10. The importance of this cytokine in regulating the immunity of the intestinal mucosa has been demonstrated by the development of IID in mice with a deficiency of IL-10 (FIOCCHI C. Inflammatory bowel disease: etiology and pathogenesis. Gastroenterology, 115: 182-205, 1998).

The clinical importance of the expression of IL-10 is supported by studies that show that the immunological increase of this cytokine prevents inflammation and damage to the mucosa, in colitis animal models and in humans. This meant that the cytokine system became an object of interest that was promising for the development of clinically relevant anti-inflammatory drugs.

It is further known that in IID and acute and chronic inflammations such as rheumatoid arthritis, SIRS and psoriasis, an imbalance occurs between pro-inflammatory and anti-inflammatory cytokines, in particular, increased levels of pro-inflammatory cytokines are detected, such as IL-1, IL-6, IL-8, IL-12, TNF-α and IFN-β, which are secreted by macrophages, lymphocytes, and polymorphonuclear neutrophils. This activity leads to an amplification of the inflammatory cascade and to the secretion of more inflammatory mediators, enzymes and free radicals that cause tissue injury and are implied in the pathogenesis of IDD alterations, such as diarrhea, mucosal permeability and fibrosis, and also in the pathogenesis of acute and chronic inflammations such as in rheumatoid arthritis.

Given the potent immunosuppressive effects of the cytokine IL-10, it began to be examined as a potentially therapeutic agent for the IID and other acute or chronic inflammatory diseases, in humans. In this context, it has been widely demonstrated that many compound derivatives of plants present significant anti-inflammatory effects. This is why they represent potential agents for the development of new drugs, especially intended for the treatment of control of chronic inflammatory states.

Matrine, for example, is an alkaloid found in plants of the Sophora genus, and proved to have anti-inflammatory effects in colitis-induced mice by trinitrobenzene sulfonic acid (TNBS), probably by regulating the production of colonic TNF-α(CHENG, H.; XIA, B.; ZHANG, L.; ZHOU, F.; ZHANG, Y. X.; YE, M.; HU, Z. G.; LI, J.; WANG, Z. L.; LI, C.; GUO, Q. S. Matrine improves 2,4,6 trinitrobenzene sulfonic acid-induced colitis in mice. Pharm. Res., 53(3): 202-208, 2005). Another example is the root extract of plants of the Poligalae (Polygala tenuifolia) genus, which is a medicinal plant that proved to have a preventive action on TNBS-induced colitis probably by regulating the production of IFN-γ and IL-4.

Moreover, the natural latex of the rubber tree Hevea brasiliensis has been studied for a long time, chiefly due to its angiogenic and healing properties. This material showed that it produced increased vascularization, epithelization, accelerating the process of granulation of chronic wounds of various etiologies and complete healing in a shorter time and at a lower cost, when compared to those available on the market.

Hence, by developing a protein preparation derivative of the latex of Hevea brasiliensis, and a composition containing it, the present invention provides desirable results in the combat and prevention of acute or chronic inflammatory diseases.

BRIEF DESCRIPTION OF THE INVENTION

In one embodiment, the present invention refers to a protein preparation derivative of the latex of Hevea brasiliensis and to compositions containing said protein preparation in low concentration, in addition to pharmaceutically acceptable vehicles, excipients or stabilizers.

Additionally, the present invention refers to the use of the protein preparation or the compositions containing it in the preparation of a medicine to treat or prevent chronic and acute inflammatory diseases, such as IID, SIRS, rheumatoid arthritis and psoriasis, and to the method of treating or preventing the same which uses the protein preparation or compositions containing it.

Following electrophoresis, it is possible to note 4 protein bands: 1) in the molecular mass 45 kDa region, 2) in the 30 kDa region, and 3) in the 20 kDa region, with dimeric behavior, as it sustains the action of reduction, disappearing from this region, moving towards the 10 kDa region.

The 20 kDa band, comprising 2 chains of 10 KDa, is probably F8, releasing interleukin 10 (IL-10). The last band is in the 10 Kda region.

Figure 3:
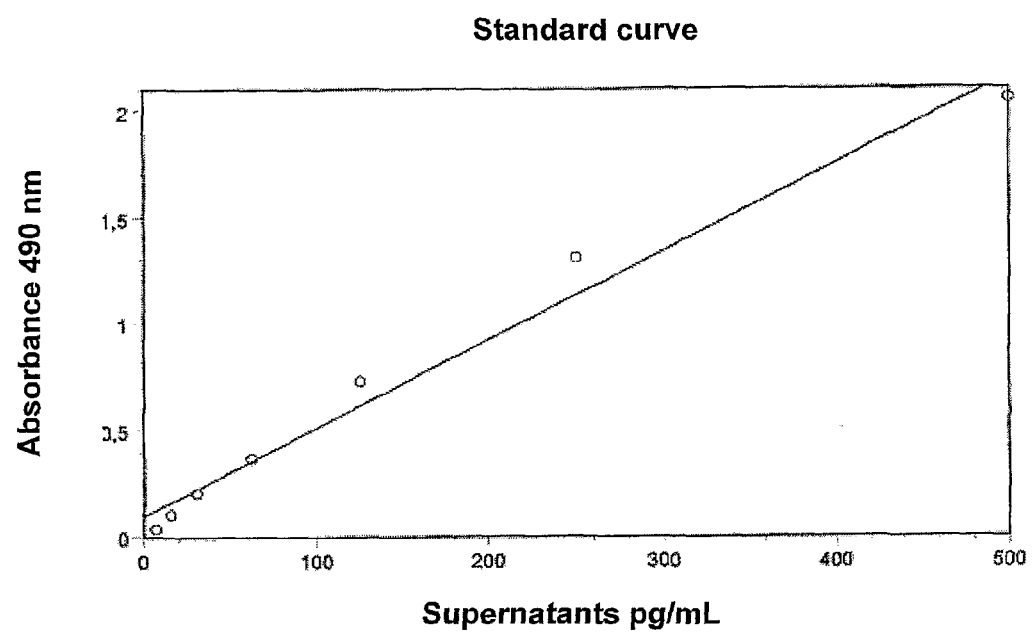

FIG. 3 depicts a standard curve of the cytokine IL-10 dosage. This standard curve was obtained through serial dilutions of cytokine IL-10 in concentrations of: 500, 250, 125, 62.5, 31.2, 15.6 and 7.8 pg/mL. The diluent, without IL-10, was used as zero standard concentration (pg/mL).

Figure 4:
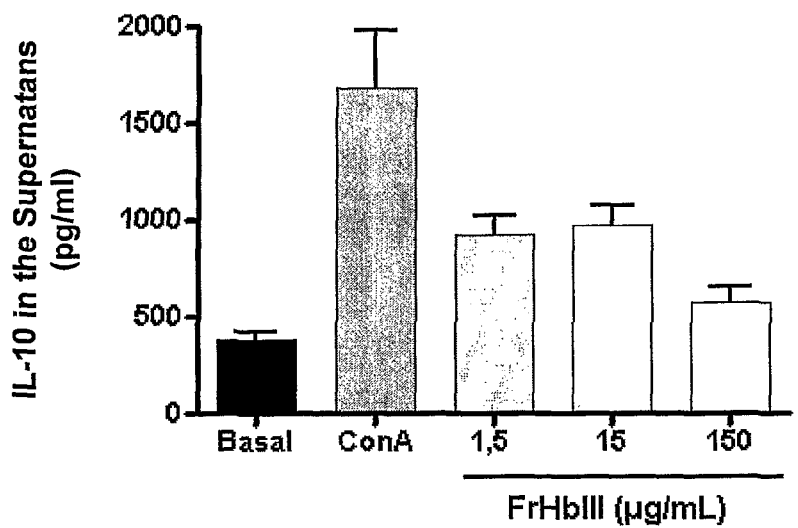

FIG. 4 depicts the levels of IL-10 (pg/mL) in the supernatants of the mononuclear cell culture cultivated only in the presence of the culture medium (Basal), in the presence of the culture medium with the addition of Concavaline A (ConA) (50 µg/mL), and in the presence of the culture medium with the addition of the protein preparation of the invention ($p<0.05$).

Figure 5:
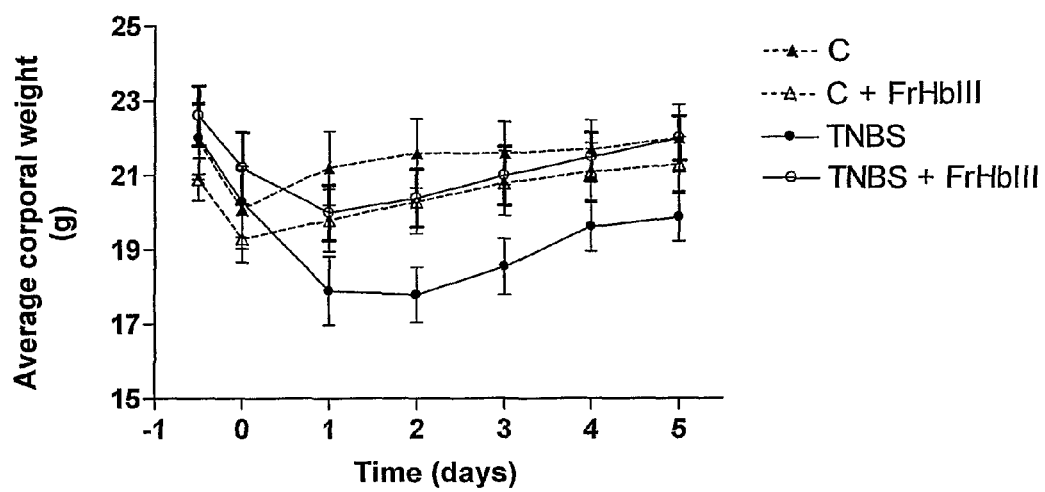

FIG. 5 depicts the weight variation of the group of control animals (C and C+protein preparation), after colitis induction (TNBS), and orally treated with the protein preparation (TNBS+protein preparation). The variation in weight indicated between the period −1 and 0 corresponds to the fasting period to which the animals were submitted prior to the experiment (12 h). The treatment of group C, C+Protein preparation, TNBS and TNBS+Protein preparation began on day 0. The graph represents the average±standard error (ASE) of the increase or weight loss which was monitored daily (n=10 animals/group).

Figure 6:
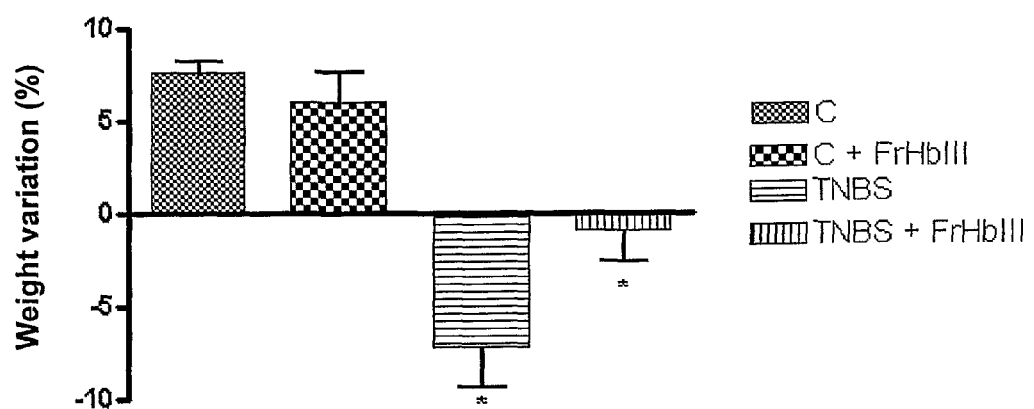

FIG. 6 depicts the weight variation in percentage (%) after colitis induction (day 0) and the $5^{th}$ day of treatment with the protein preparation. The graph represents the average±ASE of the increase or weight loss, checked daily, for the 5 days of treatment, compared to day 0. ($P<0.01$). * $P=0.01$ compared to the TNBS group (n=10 animals/group).

Figure 7:
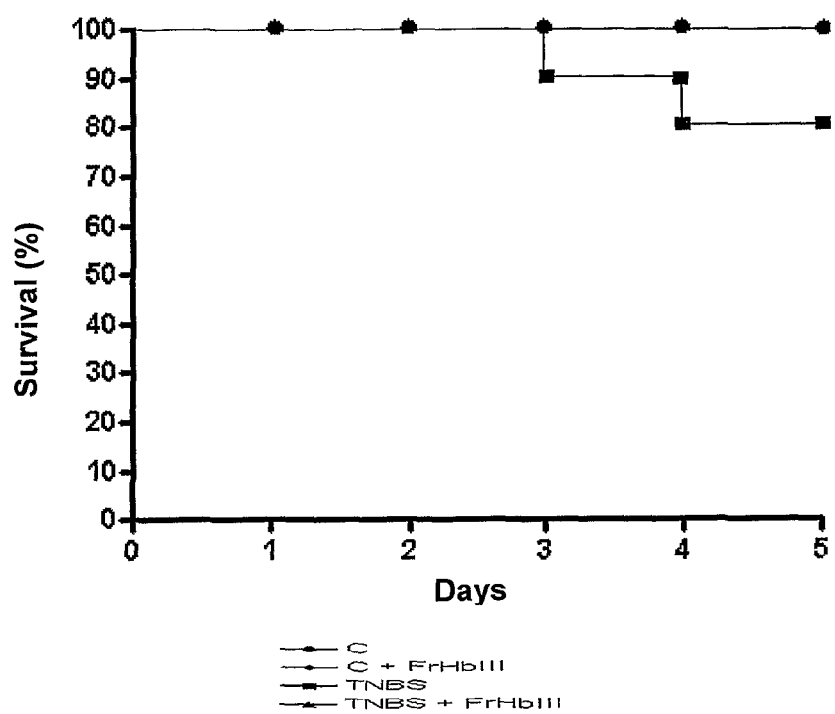

FIG. 7 depicts the survival rate of the animals after colitis induction by TNBS and treatment with the protein preparation.

Figure 8:
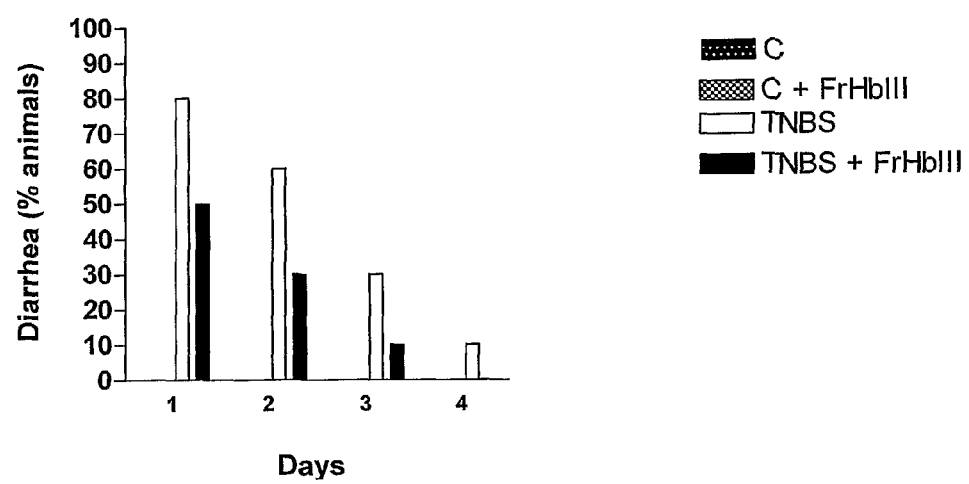

FIG. 8 depicts the percentage of animals that presented diarrhea during the experiment period. The animals of group C received the administration of ethylic acid 50% via rectal and water via oral, the animals of group C+protein preparation received the administration of ethylic acid 50% via rectal and the protein preparation diluted in water, via oral, the animals of TNBS group received the administration of TNBS diluted in ethylic acid 50% via rectal and water via oral, and the animals of TNBS group+protein preparation received the administration of TNBS diluted in ethylic acid 50% via rectal and treatment with the protein preparation diluted in water via oral.

Figure 9:
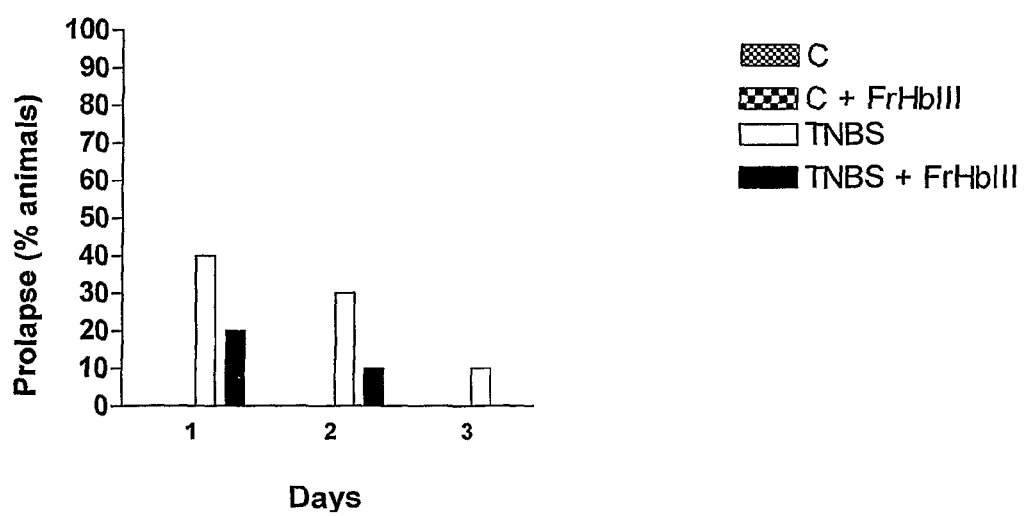

FIG. 9 depicts the percentage of animals that presented rectal prolapse during the experiment period. The animals of group C received the administration of ethylic acid 50% via rectal and water via oral, the animals of group C+protein preparation received the administration of ethylic acid 50% via rectal and protein preparation diluted in water, via oral, the animals of TNBS group received the administration of TNBS diluted in ethylic acid 50% via rectal and water via oral, and the animals of TNBS group+protein preparation received the administration of TNBS diluted in ethylic acid 50% via rectal and treatment with the protein preparation diluted in water via oral.

Figure 10:
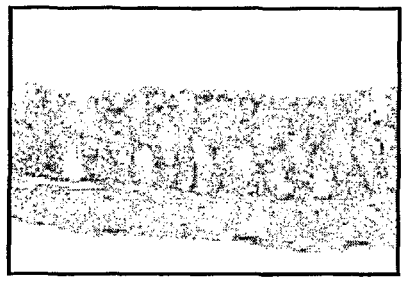
Figure 10:

FIG. 10 depicts the histological alterations found in the colon of the TNBS group in relation to the control group, stained by Hematoxylin-eosin (HE). Control Group (A) only received administration via intra-rectal of ethylic acid 50%. TNBS group (B) received administration via intra-rectal of ethylic acid 50% and trinitro benzene sulfonic acid. Pro found structural alterations caused by the colitis induction in group B were noted, with thickening of the colon wall, presence of inflammatory infiltrate, edema and deformity of the intestinal walls. Original increase: 40×.

Figure 11:
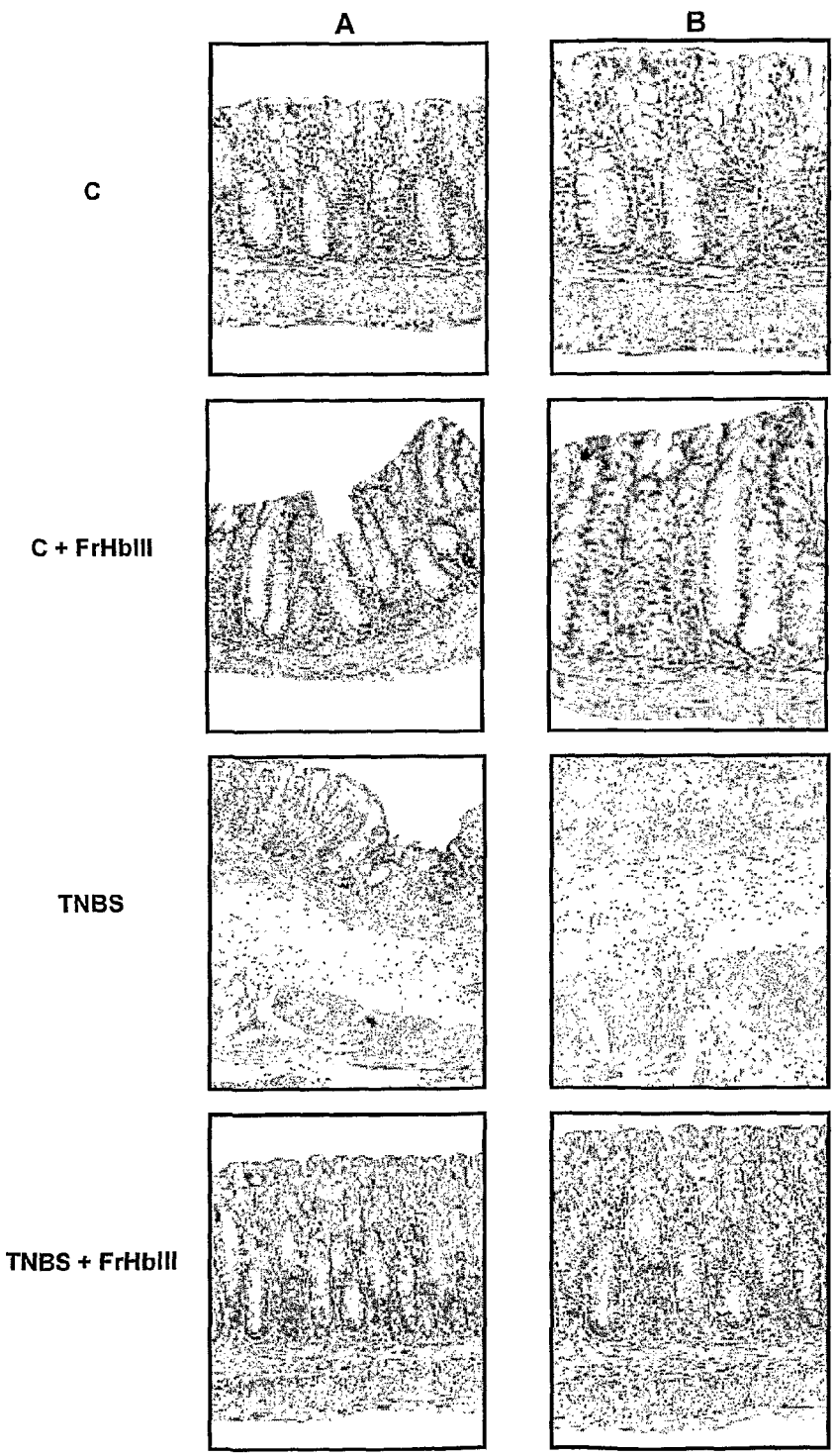

FIG. 11 depicts the histological analysis of the colon of animals with TNBS-induced colitis, treated with the protein preparation, in relation to the control groups. Control Group (C) received administration via intra-rectal of ethylic acid 50%. Control Group treated with the protein preparation (5 mg/kg) (C+protein preparation) received administration via intra-rectal of ethylic acid 50% and daily treatment with the protein preparation via oral. TNBS group (TNBS) received administration via intra-rectal of ethylic acid 50% and TNBS. TNBS group treated with the protein preparation (5 mg/kg) (TNBS+protein preparation) received administration via intra-rectal of ethylic acid 50% and TNBS and daily treatment with the protein preparation via oral. A major improvement is noted in terms of the inflammatory reaction and preservation of the tissue of the TNBS+protein preparation group in relation to the TNBS group, presenting histological characteristics very close to normality (group C). Original increase: 100× (A) and 200× (B).

Figure 12:
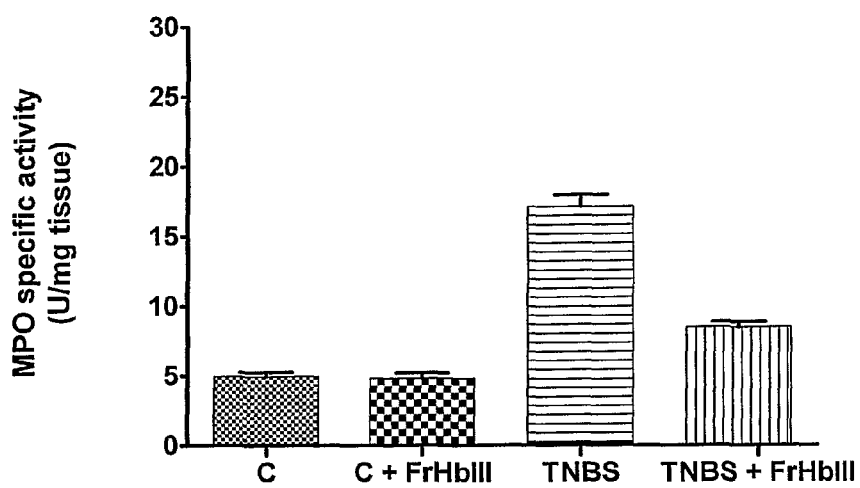

FIG. 12 depicts the average variation of the myeloperoxidase (MPO) enzyme activity between the groups at the end of the experiment ($5^{th}$ day after colitis induction). $p<0.01$. * $p<0.01$ compared to the TNBS group.

DETAILED DESCRIPTION OF THE INVENTION

The present invention refers to a protein preparation derivative of the latex of *Hevea brasiliensis* with a molecular weight lower than 60 kDa, determined by electrophoresis SDS-PAGE, as well as compositions that contain the aforementioned protein derivative in low concentrations and pharmaceutically acceptable vehicles, excipients or stabilizers.

The concentration of the protein preparation in the compositions of the invention is, preferably, lower than 15 µg/mL, more particularly is comprised between 1.5 ng/ml and 15 µg/mL.

The preparation according to the invention can be administered in solid form, for example in capsules and tablets, or in liquid form.

Suitably with the composition of the present invention, acceptable vehicles, excipients or stabilizers are non toxic in the dosages and concentrations used and include buffers such as phosphate, citrate and other organic acids, antioxidants that include ascorbic acid and metionine; preservatives (such as octadecyl dimethyl benzyl ammonium chloride, hexamethonium chloride, benzalkonium chloride, benzethonium chloride; phenolic, butylic or benzylic acid; alkyl parabens such as methyl or propyl paraben; cathecol; resorcinol; cyclohexanol; 3-pentanol; and m-cresol); low molecular weight polypeptides (less than about ten residues); proteins, such as serum albumin, gelatin or immunoglobulins; hydrophilic polymers such as polyvinylpirrolidone; amino acids, such as glycine, glutamine, asparagine, histidine, arginine or lysine; monosaccharides, disaccharides and other carbohydrates, including glucose, manose or dextrines; chelating agents, such as EDTA; sugars, such as saccharose, manitol, trehalose or sorbitol; salt-forming counter-ions such as sodium; metallic complexes (for example, complexes of Zn and protein); and/or non-ionic tensoatives, such as TWEEN®, PLURONICS® or polyethylene glycol (PEG).

The composition of the present invention may also present an enteric coating.

The compositions of the present invention that use low concentrations of the protein preparation, present excellent production results of IL-10, being highly efficient in the prevention or treatment of chronic or acute inflammatory diseases.

Furthermore, the composition of the present invention, with low concentrations of the protein preparation, was able to increase the weight of animals tested gradually, meaning the animals recovered the initial weight recorded on the day of the experiment (FIG. 5). Additionally, the animals presented low incidence of diarrhea and rectal prolapse, and 0 mortality rate.

In light of this, the administration of compositions according to the present invention implied in significant improvements in terms of clinical signs (diarrhea, rectal prolapse, weight loss) relating to colitis, indicating an anti-inflammatory activity of the protein preparation of the invention, under the specifically-applied conditions.

In another aspect, the present invention refers to the use of the protein preparation or compositions containing it in low concentrations, for treating or preventing chronic or acute inflammatory diseases, such as (ID, rheumatoid arthritis and SIRS.

Yet another object of the present invention is the use of the protein preparation or compositions containing it in low concentrations, in the preparation of a medicine to treat or prevent chronic or acute inflammatory diseases.

According to the present invention, chronic or acute inflammatory diseases include rheumatoid arthritis, systemic inflammatory response syndrome (SIRS), psoriasis and IID, such as, for example, ulcerative rectocolitis, ulcerative colitis, Crohn's disease.

The concentrations of the protein preparation or compositions used in preparing the medicine are comprised within the range of 1.5 ng/ml to 15 µg/ml ($1.5 \times 10^{-7}$ to $1.5 \times 10^{-4}$%).

The present invention also refers to a method of treating or preventing chronic or acute inflammatory diseases, such as IID, rheumatoid arthritis and SIRS, the method being characterized whereby an effective amount of the protein preparation or composition containing it in low concentrations is applied to a patient requiring treatment.

The protein preparation or compositions containing it in low concentrations can be administered by any appropriate means, including parenteral, subcutaneous, intraperitoneal, intrapulmonar, intranasal, anal, bolus and topical application. Parenteral infusions include intramuscular, intravenous, intra-arterial, intraperitoneal or subcutaneous administration. Preferably, the composition is administered orally, and present on the enteric coating.

According to the present invention, an effective amount of the protein preparation or a composition containing it in low concentrations, administered to the patient, is comprised within the range of 1.5 ng/ml to 15 µg/ml ($1.5 \times 10^{-7}$ to $1.5 \times 10^{-4}$%).

EXAMPLES

Example 1

Obtaining the Protein Preparation

Obtaining the Serum:

The natural latex was extracted from trees belonging to a single plantation, from various clones of the rubber tree *Hevea brasiliensis* (principally RRhim 600 and GT-1), through incisions in the bark at a height of 60 to 90 cm in a half-spiral shape, which received 1.5 to 2% of ammonium hydroxide, with a view to avoiding self-coagulation thereof.

Throughout the project, the material was supplied by companies from the region of Rio Preto-SP. Extracting the rubber was performed in a laboratory by adding acetic acid, and the latex serum, the protein-containing material of interest was thus obtained.

Chromatography in Ionic Exchange Column—DEAE-Cellulose (Diethylaminoethyl Cellulose):

A column of glass filled with DEAE-cellulose (5 cm×50 cm) matrix, equilibrated with buffer ammonium bicarbonate 0.01 M (pH 9.0) was used for chromatographic purification.

The quantity of proteins of latex serum was determined using the LOWRY method (Lowry O H, Rosebrough N J, Farr A L, Randall, Protein measurement with the folin phenol reagent, R J. *J Biol Chem;* 193:265-75 (1951)) modified by HARTREE (Hartree E F Determination of protein: A modification of the Lowry method that gives a linear photometric response. *Anal Biochem* 48: 422-427 (1972)), and the average concentration of the proteins of the preparations, being 0.36 mg/mL, corresponding to a total of 720 mg of total protein applied in the column (2 L of serum).

The serum had its pH adjusted to 9.0 by adding NaOH 5.0 M and was applied to the chromatographic column at ambient temperature, eluted with a buffer of ammonium bicarbonate 0.01 M in a discontinuous and crescent gradient of NaCl (0 M; 0.15 M; 0.25 M and 1.5 M of NaCl) in step-wise shape. The flow used was 7 mL/min and the eluate monitored at 280 nm in a spectrophotometer. The fractions were collected at the rate of 30 mL per tube, with the aid of a collector (Gilson®). The following was obtained with each addition of the different concentrations of sodium chlorate: $1^{st}$ peak (FrHbI) at 0.15 M, $2^{nd}$ peak (FrHbII) at 0.25 M and $3^{rd}$ peak (protein preparation—FrHbIII) at 1.5 M.

The material, according to the chromatographic profile, had its respective characteristic peaks collated and submitted to dialysis against distilled water, lyophilized and stored at −20° C., for subsequent analysis of biological activity.

Figure 1:
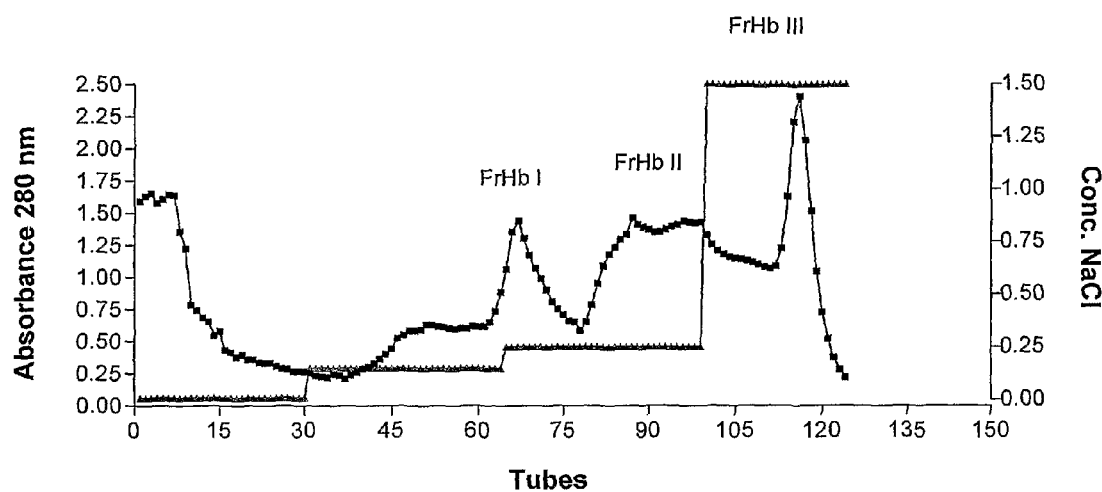
FIG. 1 depicts the chromatographic profile of 2 liters of latex serum in pH 9.0, applied to a DEAE-cellulose column (diethylaminoethyl cellulose) (5.0×50.0 cm), equilibrated with a buffer of ammonium bicarbonate 0.01M, in pH 9.0. The elution was carried out in a discontinuous and crescent gradient of sodium chlorate (0; 0.15; 0.25 and 1.5 M) using a flow of 7 ml/min. The eluate was monitored at X=280 nm. The fractions were designated FrHb I, FrHb II and FrHb III. The preparation of the invention, hereinafter referred to simply as "protein preparation", is particularly that whose composition corresponds to that found in the fraction FrHb III, wherein the proteins are heavily acidic in character, negative charge density, and molecular weight varying from 60 to 4 kDa, determined through SDS-PAGE (sodium dodecyl sulphate-polyacrylamide gel electrophoresis).
Figure 2:
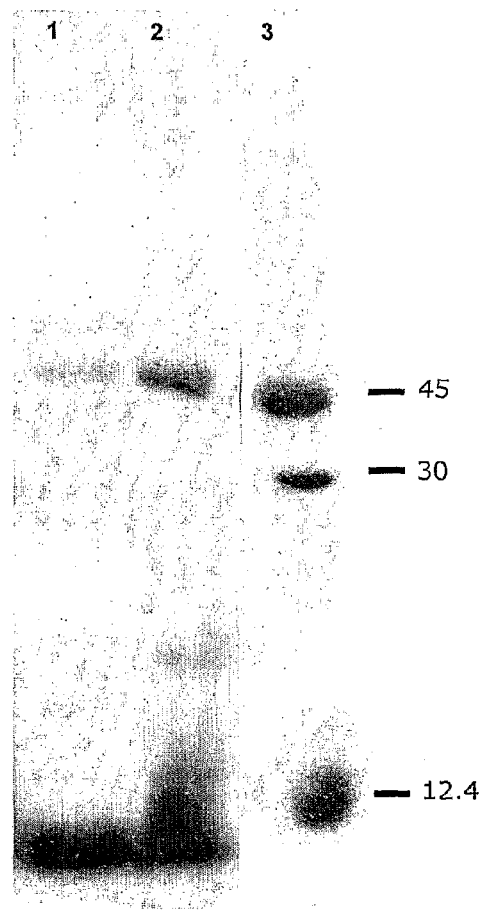
FIG. 2 depicts a polyacrylamide gel electrophoresis (PAGE) with SDS of peak 3 (fraction FrHb III) treated with SDS, and peak 3 (fraction FrHb III) treated with SDS and reduced by 2-mercaptoethanol, and a standard with known molecular mass proteins: ovoalbumin (45 kDA), carbonic anhydrase (30 kDa) and cytochrome c (12.4 kDa) was placed into a well.

The chromatographic profile obtained after complete elution of the material and monitoring the profile by spectrophotometric reading of the absorbance in the wave length ($\lambda=280$ nm) is illustrated by FIG. 1.

Next, the fraction FrHBIII, representative of the protein preparation of the invention, was submitted to evaluation tests for anti-inflammatory activity in model in vivo.

Example 2

Evaluation of the Production of Cytokine of IL-10 in Samples of Human Mononuclear Cells in the Presence of the Protein Preparation Peripheral Blood Collection:

Blood was collected from voluntary donors after explaining the objectives of the study and obtaining written authorization.

Samples of 15 mL of venous blood were collected from each donor, obtained by puncturing the brachial vein, following asepsis with iodated alcohol.

Obtaining the Cells:

To separate the mononuclear cells, the blood collected was immediately diluted with the same volume of culture medium (RPMI 1640) and the solution obtained was placed on the gradient Ficoll—Hipaque®. These cells were cultivated according to the protocol previously established by Cell Culture Laboratories.

The method was developed under sterile conditions, using a laminar flow chamber. Ten (10) mL of diluted blood was slowly and carefully pipetted into a 15 mL polypropylene tube, containing 3 mL of Hystopaque. The preparation was centrifuged at 400×g for 30 minutes to form 4 distinct layers: superior, containing plasma, culture medium RPMI (Roswell Park Memorial Institute) and platelets; interface, containing mononuclear cells; average, gradient Ficoll-Hipaque®; and inferior, granulocytes and red blood cells.

The layer of mononuclear cells was resuspended in 10 mL of isotonic saline solution and centrifuged at 350×g for 10 minutes. The supernatant was discarded and the process was repeated twice. The pellet was resuspended in 1.0 mL of culture medium. After evaluating the viability of the mononuclear cells, with Trypan blue solution at 0.2%, the cells were counted under an optical microscope with the assistance of a Neubauer camera, following the dilution 1:20 (v/v) in Turk color. The cell suspension was diluted in a culture medium enriched with 10% of fetal bovine serum (FBS) to obtain a concentration of $2.5 \times 10^6$ cells/mL.

Quantitative Methodology—ELISA:

The ELISA immunoenzymatic test was used to quantify the cytokine IL-10. Culture dishes of 96 wells sterilized by $\gamma$ radiation were used, and the mononuclear cell cultures prepared in the concentration of $1.5 \times 10^6$ cells/mL containing 10% of fetal bovine serum (FBS) per well. Cell cultures containing only the culture medium were made to control the spontaneous cell proliferation (Basal), and duplicates containing culture medium and 100 µL of Concavaline A mitogene (50 µg/mL—Sigma®) were made to control the stimulus to proliferation.

Serial dilutions (1:10 v/v) were made of the protein preparation obtained from chromatography of the latex in DEAE-cellulose, sterilized by filtration in filters of 0.23 µm, in a sterile culture medium RPMI, in order to obtain the concentrations of 150 µg/mL, 15 µg/mL and 1.5 µg/mL. The respective dilutions (150 to 1.5 µg/mL) of the protein preparation were added in volume of 100 µL to the corresponding wells.

Further tests were performed with more diluted concentrations from 1.5 ng/ml to 15 µg/ml.

The dishes were then placed in automatic cell culture greenhouse with humid atmosphere with $CO_2$ 5%, at 37° C. for 72 hours. After the incubation period, the supernatants of these cultures were collected and stored in microtubes at −20° C. for subsequent dosage of cytokine IL-10.

The supernatants of the mononuclear cell cultures were thawed at ambient temperature, centrifuged at 1200 rpm for 1 minute and diluted (10 times) for the dosage of IL-10 at the moment of the experiment.

Preparation of the Standard Curve:

The standard curve was obtained from serial dilutions of IL-10 (kit BD OptEIA™ Set Human IL-10, BD Biosciences Pharmigen—USA) in concentrations of: 500, 250, 125, 62.5, 31.2, 15.6 and 7.8 pg/mL. The diluent, without IL-10, was used as zero standard concentration (pg/mL). A dish with 96 wells was used, using the first column of the dish for the standard curve. After diluting the Antibody (Ac) of capture (clone JES3.19F1. Isotype: Rat IgG2a) purified (1 µL/mL) for IL-10, 50 µL of the solution per well was added, followed by an incubation period of 16 hours at 4° C. The dish was returned to ambient temperature and 200 µL of the blockage buffer per well was added, incubating again for 2 hours at the same temperature. Each well was aspirated and washed 4 times. Next were added to the serial dilutions of the IL-10 standard in the first column, the cell suspensions of cells cultivated with Concavaline A (ConA) in column 2, and the supernatants obtained from the culture diluted in buffer in the other columns, using 100 µL per well. The dish was incubated for 16 hours at 4° C. Next the dish was washed 5 times. Next was added 100 µL of detection Ac (anti IL-10) biotinylated (1 µg/mL—Clone JES3.12G8. Isotype: Rat IgG2a) in blockage buffer Tween and the dish was incubated for 1 hour at ambient temperature. The washing procedure was repeated a further five times. Next was added 100 µL of HRP (conjugated enzyme) diluted 1000 times incubating the dish for 30 minutes at ambient temperature. The washing procedure was again repeated five times. Next was added 100 µL of the colored reagent o-phenylenediamine/Sigma® (OPD) diluted in its own buffer protected from light, and the dish was incubated for 10 minutes. Fifty (50) µL of "stop" solution ($H_2SO_4$ at 16%) were added in each well to interrupt the reaction, obeying the same placement sequence of the substrate solution. The optical density was determined in the subsequent 30 minutes, in a wavelength of 490 nm using the ELISA (Titertek Muiltiskan MCC/340) reader. The entire experiment was performed in duplicate.

The standard curve of the quantification of IL-10 by ELISA under the experimental conditions described above is illustrated in FIG. 3.

Further, the quantification of the cytokine IL-10 in the supernatants obtained from the mononuclear cell cultures of the peripheral blood, under basal condition (no stimulus), stimulated by Concavaline A, and treated with the protein preparation is illustrated in FIG. 4.

It is noted in FIG. 4 that the presence of the protein preparation significantly induced the release of the cytokine IL-10 (pg/mL; $p<0.05$) in the concentrations 1.5 and 15 µg/mL in relation to the basal release. A significant decrease in the release in the concentration 150 µg/mL can be observed, likely due to cytotoxic and/or anti-proliferative effects.

The results of quantifying the cytokine IL-10 set forth refer to an initial project based on the evaluation of this cytokine in the different concentrations of the protein preparation.

Example 3

Evaluation of the Anti-Inflammatory Activity of the Protein Preparation Using the Model of Experimental Colitis in Mice Experiment Animals:

Female Balb-c mice aged 2 to 4 months were used. The animals were divided into 4 groups, each containing 10 animals: Control (C): comprised of animals which received the administration of the vehicle ethylic acid 50% via rectal and 0.5 mL of water administered by gavage, with the assistance of a cannula PE 10 coupled to a 1.0 mL syringe, via oral; Control (C)+protein preparation: comprised of animals which received the vehicle ethylic acid 50% via intra-rectal and treatment with protein preparation (5.0 mg/Kg), diluted in 0.5 mL of water via oral; TNBS: comprising animals which received the administration of TNBS diluted in ethylic acid 50% via rectal and 0.5 mL of water via oral; and TNBS+ protein preparation: comprising animals which received the administration of TNBS diluted in ethylic acid 50% via rectal just like TNBS, but submitted to treatment with protein preparation (5.0 mg/Kg), diluted in 0.5 mL of water via oral.

The mice were kept within the normal standards of temperature, humidity and light/dark (12 h/12 h) cycle, with free access to food and water "ad libitum".

Colitis induction: Colitis was induced according to the method previously described by NEURATH et al. (NEURATH, M. F.; FUSS, I.; KELSALL, B. L.; STÜBER, E.; STROBER W. Antibodies to interleukin 12 abrogate established experimental colitis in mice. J Exp Med., 182: 1281-1290, 1995), with changes. The mice were deprived of food 12 hours before the experiment, receiving just water ad libitum.

For colitis induction, the animals were previously anesthetized with a solution containing: Ketamin—S(+) (50 mg/mL, Cristália®) and Dopaser (xylazin 20 mg/mL, Caere), dose 400 μL/20 g animal, via intraperitoneal. In the TNBS and TNBS+protein preparation groups, colitis was induced through slow rectal administration of 5.0 mg of TNBS in 0.1 mL of ethylic acid 50%, with the aid of a silicone cannula adapted in a 1.0 mL syringe, such that the end of the cannula is positioned at about 4 cm from the anus. The Control and Control (C)+protein preparation groups received, as described above, only rectal administration of 0.1 mL of the vehicle ethylic acid 50%. The animals were then kept in a vertical position for about 2 minutes and returned to their boxes. Two hours after colitis induction and daily for 5 days, the animals of groups C+protein preparation and TNBS+ protein preparation received oral administration of 5 mg/Kg of the protein preparation, diluted in 0.5 mL of water by gavage. The animals of the Control and TNBS groups received 0.5 mL of water orally.

Monitoring the Animals:

To verify whether administration of the protein preparation after colitis induction would lead to clinical alterations, the animals of all the groups were weighed with the aid of electronic scales (Toledo®) and visually inspected, daily, to check for diarrhea and rectal prolapse. The percentage of weight variation on the fifth day was individually calculated for each animal, and subsequently for each group, in relation to the weight on day 0 (day of the colitis induction).

The results noted for the 5 days of treatment are represented in FIGS. 5 and 6, as discussed below.

a) Variation in Weight after Colitis Induction:

the variation of the weight obtained daily from the animals of Control groups, Control treated with the protein preparation, TNBS and TNBS treated with the protein preparation is illustrated in FIG. 5. The changes in the individual weight of the animals of each group were recorded on a daily basis.

As shown in FIGS. 5 and 6, the control group which received the administration of just ethylic acid 50% gained body weight. The animals of TNBS group—which received just the administration of water orally—lost body weight gradually over the first days after colitis induction, and began gradually recovering weight as of the third day, but by the fifth day of the experiment, they had not yet recovered the initial weight corresponding to the day of experiment (day 0). Moreover, the animals of TNBS group+protein preparation— which received treatment via oral with the protein preparation (5 mg/kg)—lost body weight only on the first day after colitis induction, gradually recovering the weight to the point of reaching the initial weight corresponding to day 0, coming close to the weight noted during the period of 12 hours that preceded the experiment (fasting period). The animals of group C and C+protein preparation gained body weight gradually throughout the whole experiment period, reaching the average body weight noted in the period preceding the fasting.

FIG. 6 represents the variation of body weight obtained during the 5 day experiment, in relation to the day 0. A significant weight increase was noted in the animals of control Group (C) and control treated with the protein preparation (C+protein preparation), without a significant differences between the groups. A significant decrease was observed in the body weight of the animals submitted to colitis induction by TNBS ($p \leq 0.01$) in relation to the animals of the control groups. Ac (anti IL-10) biotynilated However, it was noted that the group that was colitis induced by administration of TNBS and which received oral treatment with the protein preparation, although they presented significantly greater weight loss during the 5 day experiment, in relation to the control groups ($p \leq 0.01$), showed a significant weight recovery compared to the TNBS group ($p = 0.01$).

b) Survival Rate:

The survival rate of the animals after colitis induction by TNBS and treatment with the protein preparation is illustrated in FIG. 7. It can be noted that colitis induction by administering the TNBS solution resulted in a rate of up to 20% of mortality in the TNBS group after 5 days of the experiment.

Nevertheless, the group which received treatment with the protein preparation after colitis induction, presented zero mortality rate, as occurred in the C and C+protein preparation groups.

c) Diarrhea:

The percentage of animals which presented diarrhea during the experiment period is illustrated in FIG. 8. The animals of group C received the administration of ethylic acid 50% via rectal and water via oral, the animals of group C+protein preparation received the rectal administration of ethylic acid 50% and the protein preparation diluted in water orally, the animals of TNBS group received the rectal administration of TNBS diluted in ethylic acid 50% and water orally, and the animals of TNBS group+protein preparation received the rectal administration of TNBS diluted in ethylic acid 50% and treatment with the protein preparation diluted in water orally.

d) Rectal Prolapse:

The percentage of animals that presented rectal prolapse during the experiment period is illustrated in FIG. 9. The animals of group C received the administration of ethylic acid 50% via rectal and water via oral, the animals of group C+protein preparation received the administration of ethylic acid 50% via rectal and the protein preparation diluted in water, via oral, the animals of TNBS group received the administration of TNBS diluted in ethylic acid 50% via rectal and water via oral, and the animals of TNBS group+protein preparation received the administration of TNBS diluted in ethylic acid 50% via rectal and treatment with the protein preparation diluted in water via oral.

The appraisal of the animals submitted to colitis induction (TNBS group) revealed that they developed severe diarrhea (FIG. 8) and rectal prolapse (FIG. 9) on a significantly larger scale than the animals who received treatment with the protein preparation (TNBS group+protein preparation). No occurrence of diarrhea and rectal prolapse was observed in the Control and C+protein preparation groups.

Histopathological Analysis:

to determine whether the clinical alterations (diarrhea, rectal prolapse and weight loss) observed in the animals of the TNBS and TNBS+protein preparation groups, were related to any histopathological alteration, or even to tissue damage in the intestine of the animals analyzed, segments of the distal colon were sectioned, fixed and processed for histological analysis.

The mice were sacrificed by cervical dislocation and had their intestines surgically excised, being sectioned about 2.0 cm from the distal colon of each animal. To evaluate the inflammatory process, the parts were fixed in buffered formalin 10%, included in paraffin, sectioned and stained by hematoxylin-eosin (HE). The histological analysis of the sections was performed by using an optical microscope (Nikon Eclipse E800; Nikon Inc, Melville, N.Y.), with increases of 40, 100 and 200×. Images were obtained by a digital camera (Nikon DXM1200; Nikon Inc, Melville, N.Y.).

It is noted in FIG. 11 that the colon of the animals of control group (C), as well as the control group treated with the protein preparation (C+protein preparation) presented a histological aspect compatible with normality, showing an epithelium with a large number of crypts disposed side-by-side and extremely rich in caliciform cells, own blade with normal aspect and without visible hemosiderin pigments. At the base of the crypts is the muscular blade of the mucosa, followed by the submucosa, both showing no signs of inflammation. Immediately below it is noted that the circular and longitudinal extracts of the muscular tunics and, finally, the serous cover, present histological aspects corresponding to normality.

The colon of the TNBS group presented important histological alterations in its various layers (FIGS. 10 and 11), such as extensive edema of the submucosa, general disorganization of the crypts with marks where they were almost totally destroyed. There is a visible reduction of the caliciform cells and intense infiltration of inflammatory cells in the mucosa and submucosa, and it is easy to distinguish the infiltration of polymorphonuclear leukocytes. At some points, the muscular layer of the mucosa is discontinued, with the occurrence of an intense infiltration of lymphocytes, which extends up to the muscular layers. An increase in the number of vases and clearly hemorrhaged areas is notable. Ulcerations occur throughout the submucosa, extending to the muscular layers and, at some sites, it even affects the serous cover. In short, there is severe colitis characterized by destruction of crypts, reduction of the caliciform cells, extensive edema, foci of hemorrhagic ulceration, intense and diffuse infiltration of neutrophils and lymphocytes in the mucosa and submucosa, and necrose focal of the muscular strates.

However, the histopathological analysis of the colon of the animals of TNBS group+protein preparation (FIG. 11) enables the confirmation that the treatment with the protein preparation (5 mg/kg) significantly reduced the extent and severity of the histological alterations described in the TNBS group. Although it is possible to note a discrete quantity of infiltration of polymorphonuclear leukocytes, indicating the persistence of inflammatory characteristics in the colon, the crypts are well preserved and the number of caliciform cells is equal or very close to normality. No ulcers were noted and the muscular covers are whole and apparently unaltered (FIGS. 10 and 11).

Evaluation of the Myeloperoxidase (MPO) Enzyme Activity:

it is known that the MPO enzyme is expressed in high levels in polymorphonuclear leukocytes. Therefore, the accumulation of these cells in the region of an injury is a characteristic of the inflammatory process, and the quantification of the MPO enzyme is used to estimate the intensity of the inflammatory infiltrate present in damaged tissues.

Accordingly, the activity of the MPO enzyme was determined according to the method previously described by BRADLEY et al. (BRADLEY, P. P.; PRIEBAT, D. A.; CHRISTENSEN, R. D.; ROTHSTEIN, G. Measurement of cutaneous inflammation: estimation of neutrophil content with an enzyme marker. J. Invest. Dermatol., 78: 206-209, 1982), with changes.

A segment of approximately 50 mg of distal colon tissue of each animal, from each of the animal groups, was withdrawn, washed with ice-cold saline, sectioned into small fragments and frozen at −70° C. Subsequently, the fragments were homogenized in 5.0 mL of buffer of monobasic potassium phosphate 50 mM, pH 7.4, ice-cold, with the assistance of a polytron (KINEMATICA AG) 3 times for 30 seconds in each cycle. The homogenates were submitted to centrifugation (SORVAL RC-5B) for 30 minutes at 12000×g and 4° C. The supernatants were discarded and the precipitates were resuspended in 1.0 mL of buffer of monobasic potassium phosphate mM, pH 6.0, containing hexadecyl trimethyl ammonium bromide (HTABr) 0.5% (p/v). The suspensions were submitted to a quick freezing cycle (−70° C.) and unthawing (25° C.), followed by sonication with the assistance of a sonicator (Vibra Cell®) for 15 seconds for each cycle. The samples were centrifuged (EPPENDORF CENTRIFUGUE 5417R CE) for 20 minutes at 14000×g and 4° C. The supernatants were collected and stored at −70° C. An amount of 0.1 mL of the supernatant from each sample was added to 2.9 mL of the buffer of monobasic potassium phosphate 50 mM, pH 6.0, containing O-dianisidine hydrochloride (O-da) (0.167 mg/mL) and hydrogen peroxide (0.0005% v/v), and the MPO activity of the samples was evaluated by spectrophotometer reading (Hitachi® U-2000) at 460 nm and 25° C. The change in the absorbance was recorded at intervals of 30 seconds for 3 minutes. A unit (U) of the specific activity of the MPO enzyme is given by the degradation of 1 µmol of $H_2O_2$ in $H_2O$ and $O^-$ by the enzyme per minute at 25° C., and the final value of the MPO activity expressed in unit per gram of wet tissue (U/g). Calculating this activity is carried out as follows: Activity MPO (U/g)=($A_{460}$)×13.5/wet tissue (in grams); wherein $A_{460}$ is the variation in absorbance at 460 nm between 1 and 3 minutes after the start of the reaction. The coefficient 13.5 was empirically determined such that 1 unit (U) of MPO activity represents the quantity of enzyme that will reduce 1 µmol of peroxide per minute.

The results obtained demonstrate the variation of the activity of the enzyme myeloperoxidase, quantified on the $6^{th}$ day of experiment (day 5), in colon segments of the animals of the experimental groups (FIG. 12).

It is noted that the specific activity of the myeloperoxidase (MPO) enzyme was significant (p<0.01), and about four times greater in the TNBS group in relation to the C and C+protein preparation groups, indicating large quantity of acute inflammatory infiltrate. However, the group that received treatment with the protein preparation after colitis induction (TNBS+protein preparation) presented a significant reduction of the MPO activity in relation to the TNBS group, indicating the effectiveness of the treatment, and a brief increase of the significant activity ($p<0.01$) when compared to the control groups, indicating the presence of inflammatory infiltrate, but in a small quantity.

The data set forth above are corroborated by FIG. 11, where it is possible to note an intense presence of inflammatory infiltrate in the histological cuts of the animal colons wherein colitis was induced by administering TNBS, in contrast with the slight presence of inflammatory infiltrate in the histological cuts of the animals of group wherein colitis was induced by TNBS and received oral treatment with the protein preparation.

Statistical Analysis:

The data for evaluating the difference between the processes of intestinal inflammation between the experimental and control groups were performed by analyzing the "ANOVA one-way" variance (method of Dunnett's). Evaluating the activity of the enzyme myeloperoxidase was performed by analyzing the ANOVA variance according to "Bonferroni's test". Statistically significant differences were considered when $p<0.05$.

The information set forth herein enable a person skilled in the art to reproduce the invention claimed ahead exactly as shown herein or in equivalent embodiments not expressly indicated, but contained within the principles revealed and, therefore, protected in said claims.

The invention claimed is:

1. A composition comprising:
   a non-allergenic protein preparation, extracted from latex of *Hevea brasiliensis*; and
   material selected from a group consisting of pharmaceutically acceptable vehicles, excipients, stabilizers and combinations thereof, wherein the concentration of the protein preparation in the composition is less than 15 µg/mL, the protein preparation comprising acidic proteins having a negative charge density, and molecular weight less or equal to 60 kDa, wherein the protein preparation is prepared with chromatographic purification of the latex, the protein preparation providing a spectrophotometric absorbance peak at 280 nm upon spectrophotometric monitoring of a chromatograph profile of the protein preparation at 1.5 moles of NaCl when eluted with 0.01 molar ammonium bicarbonate through a diethylaminoethyl cellulose chromatographic column.

2. The composition according to claim 1, wherein the concentration of the protein preparation is between 15 ng/ml and 15 µg/mL.

3. The composition according to claim 1, wherein the composition is in solid or liquid form.

4. The composition according to claim 1, wherein the acceptable vehicles, excipients or stabilizers are selected from the group consisting of buffers, antioxidants, preservatives, alkyl parabens, cathecol, resorcinol, cyclohexanol, 3-pentanol, m-cresol, low molecular weight polypeptides, proteins, hydrophilic polymers, amino acids, monosaccharides, disaccharides and other carbohydrates, chelating agents, sugars, salt-forming counter-ions, and non-ionic tensoactives.

5. The composition according to claim 1, comprising an enteric coating.

6. A medicine effective for treatment of acute or chronic inflammatory diseases comprising a composition according to claim 1.

7. The medicine according to claim 6, wherein the diseases are intestinal inflammatory diseases selected from the group consisting of ulcerative rectocolitis, ulcerative colitis, and Crohn's disease.

8. The medicine according to claim 6, wherein diseases are inflammatory diseases selected from the group consisting of psoriasis, rheumatoid arthritis and systemic inflammatory response syndrome.

9. A medicine effective for treatment of acute or chronic inflammatory diseases comprising a non-allergenic protein preparation according to claim 1 derived from latex of *Hevea brasiliensis*, wherein the protein preparation comprises acidic proteins having a negative charge density, and molecular weight less or equal to 60 kDa.

10. The medicine according to claim 9, wherein the diseases are intestinal inflammatory diseases selected from the group consisting of ulcerative rectocolitis, ulcerative colitis, and Crohn's disease.

11. The medicine according to claim 9, wherein the diseases are inflammatory diseases selected from the group consisting of psoriasis, rheumatoid arthritis and systemic inflammatory response syndrome.

12. The medicine according to claim 6, wherein the concentration of the composition is between 1.5 ng/ml and 15 µg/ml.

13. The medicine according to claim 6, wherein the concentration of the composition is between $1.5 \times 10^{-7}$ and $1.5 \times 10^{-4}\%$.

14. The medicine according to claim 9, wherein the concentration of the protein preparation is between 1.5 ng/ml and 15 µg/ml.

15. The medicine according to claim 9, wherein the concentration of the protein preparation is between $1.5 \times 10^{-7}$ and $1.5 \times 10^{-4}\%$.

16. A method of treatment of acute or chronic inflammatory diseases, comprising administering to a subject of treatment the composition according to claim 1.

17. The method according to claim 16, wherein the diseases are intestinal inflammatory diseases selected from the group consisting of ulcerative rectocolitis, ulcerative colitis, and Crohn's disease.

18. The method according to claim 16, wherein the diseases are inflammatory diseases selected from the group consisting of psoriasis, rheumatoid arthritis and systemic inflammatory response syndrome.

19. A method of treatment of acute or chronic inflammatory diseases comprising administering to a subject of treatment a protein preparation according to claim 1.

20. The method according to claim 19, wherein the diseases are intestinal inflammatory diseases selected from the group consisting of ulcerative rectocolitis, ulcerative colitis, and Crohn's disease.

21. The method according to claim 19, wherein the diseases are inflammatory diseases selected from the group consisting of psoriasis, rheumatoid arthritis and systemic inflammatory response syndrome.

* * * * *